(12) United States Patent
Braumann et al.

(10) Patent No.: US 6,486,957 B1
(45) Date of Patent: Nov. 26, 2002

(54) REPLACEABLE FILTER MODULE

(75) Inventors: David W. Braumann, Spring Green, WI (US); Patrick J. Saunders, Waunakee, WI (US); John A. Luckey, Merrimac, WI (US); Robert L. Brumley, Jr., Mazomanie, WI (US)

(73) Assignee: GeneSys Technologies, Inc., Sauk City, WI (US)

( * ) Notice: Subject to any disclaimer, the term of this patent is extended or adjusted under 35 U.S.C. 154(b) by 0 days.

(21) Appl. No.: 09/396,571

(22) Filed: Sep. 15, 1999

Related U.S. Application Data

(60) Provisional application No. 60/100,308, filed on Sep. 15, 1998.

(51) Int. Cl.⁷ .............................................. G01N 21/25
(52) U.S. Cl. ...................... 356/416; 356/301; 356/417; 356/411
(58) Field of Search ................................ 356/416, 419, 356/418, 311, 301, 344, 411; 250/226

(56) References Cited

U.S. PATENT DOCUMENTS

| | | | |
|---|---|---|---|
| 4,654,698 A | * 3/1987 | Langworthy | 358/43 |
| 4,776,702 A | * 10/1988 | Yamaba | 356/405 |
| 5,538,613 A | 7/1996 | Brumley et al. | |
| 5,981,956 A | * 11/1999 | Stern | 250/458.1 |
| 5,995,235 A | * 11/1999 | Sui et al. | 356/419 |
| 6,013,168 A | * 1/2000 | Arai | 204/601 |
| 6,064,897 A | * 5/2000 | Lindberg et al. | 600/316 |

* cited by examiner

*Primary Examiner*—Frank G. Font
*Assistant Examiner*—Layla Lauchman
(74) *Attorney, Agent, or Firm*—Quarles & Brady LLP

(57) ABSTRACT

An instrument for processing light information to assay chemical or biological molecules is made more flexible by the use of a replaceable filter module. Several light filters, or in one embodiment dichroic mirrors, are mounted in a common module in fixed position relative to each other. The whole filter module can then be removed, and a different one inserted in its place, to change the wavelength bands of light detected by the instrument, as needed, for different applications.

17 Claims, 9 Drawing Sheets

REPLACEABLE FILTER MODULE

CROSS-REFERENCE TO RELATED APPLICATIONS

This application claims the benefit of U.S. Provisional Application No. 60/100,308, filed Sep. 15, 1998.

STATEMENT REGARDING FEDERALLY SPONSORED RESEARCH OR DEVELOPMENT

Not applicable.

BACKGROUND OF THE INVENTION

Many optical systems utilize spectrum separation techniques and light diversion systems to select one or more wavelength bands of light and to direct the selected light to a sensing device. In many different types of instrumentation, often a specific spectrum of light is what is selected, because the signal sought to be detected is spectrum limited. For example, in many chemical analytical instruments, the distinguishing characteristics of a chemical mixture are detected by sampling the wavelengths or wavelength bands of light originating from a chemical or biological sample. In a simple example, a single distinct species of molecule that emits light in a characteristic wavelength can be identified by a detection system that selectively collects and transmits that wavelength band to a photodetector. When mixtures of chemicals, each with a specific light-emitting characteristic, are mixed, it then becomes necessary to enable multi-color transmission and detection, as well as separation.

Instrument designs to accomplish multi-color detection rely on optical elements such as color filters, gratings and dichroic mirrors to separate an incident light signal into one or more light signals that each encompasses a characteristic wavelength band. Light signals contained within selected wavelength bands can then be analyzed by photodetectors to determine the intensity of light present in the incident light beam in one or more wavelength regions. Such analysis can reveal the chemical components of the sample under study.

Multi-color systems are known which use dichroic mirrors to define the wavelength regions to be analyzed. FIG. 1 illustrates a simple system, known to the prior art, that uses three dichroic mirrors in a row to separate incident light into three primary colors. This system is used in electronic color imaging such as described in U.S. Pat. No. 4,654,698 to Longworthy. FIG. 2, also illustrating a prior art system, illustrates the type of system used in U.S. Pat. No. 3,7944,407 to Nishimura that includes two dichroic mirrors and three photodetectors. This systems uses an additional filter in front of each photodetector to further define the wavelength region being detected. Systems using three dichroic mirrors and four photodetectors, exemplified by U.S. Pat. No. 4,776,702 to Yamaba and U.S. Pat. No. 5,538,613 to Brumley, are illustrated schematically in FIGS. 3 and 4 respectively.

In all of these systems, the dichroic mirrors are used to reflect a desired wavelength band of light to a detector or group of detectors while the non-selected wavelength bands are directed to other dichroic mirrors. In all of these designs, the dichroic mirrors are fixed in place, thus limiting the instrument to the detection of light patterns of certain defined characteristics. In short, the instruments are dedicated to a defined type or pattern of light sensing.

In some applications, notably for the detection of fluorescently tagged DNA molecules, it would be desirable in different applications to be able to filter and detect different wavelength bands. For DNA sequencing procedures, a set of fluorescent dyes are commonly used to tag the DNA molecules so that the sequence of the DNA molecule can be detected by optical reading. For other DNA analysis procedures, for a variety of reasons not important here, the use of different fluorescent tags which have a different spectral characteristic, are more desirable. Therefore, an instrument which is capable of altering its optical characteristics for the particular application would be adapted for use in more applications, as contrasted to one that was invariable in it optics.

BRIEF SUMMARY OF THE INVENTION

The present invention is summarized in an apparatus using light signals to test chemical properties of a sample, that the apparatus includes a reasonable filter module which includes a plurality of dichroic mirrors each of which is fixed in place relative to the other mirrors in the filter module, so that filter modules can be changed in the instrument to permit the optical characteristics of the instrument to be changed without the need for mirror adjustments of the mirrors relative to each other.

It is an advantage of the present invention that it enables devices intended for analysis of DNA molecules to be used for a variety of different applications which use a variety of fluorescent tags.

It is a feature of the present invention that it enables optical instruments of greater versatility for chemical or biochemical analysis.

Other objects, advantages, and features of the present invention will be apparent from the following specification, when taken in conjunction with the accompanying drawings.

DETAILED DESCRIPTION OF THE INVENTION

The present invention makes use of a removable filter module for use in an instrument for detecting fluorescence from molecules, or for other instruments utilizing multispectrum light for information gathering. In its initial application, the present invention is intended to be an improvement to the type of device described in U.S. Pat. No. 5,538,613 to Brumley, the specification of which is hereby incorporated herein by reference. In summary, an instrument of that type is one in which fluorescently labeled DNA molecules move within an electrophoresis gel and are then detected optically. The light from the DNA gel is transmitted through a series of dichroic mirrors. As used herein, a dichroic mirror is one in which light of a limited range of wavelength, typically defined as a center wavelength of transmission with a certain full width at half-maximum, is transmitted through the mirror while wavelengths outside of this transmission band are reflected off of the dichroic mirror's surface. Wavelengths of light that are not transmitted through the dichroic mirror are reflected with high efficiency, exceeding 98%. So the dichroic mirror is, in essence, a sort of band-pass filter permitting light of a defined wavelength band to pass through it while the remaining light is reflected.

Figure 1:
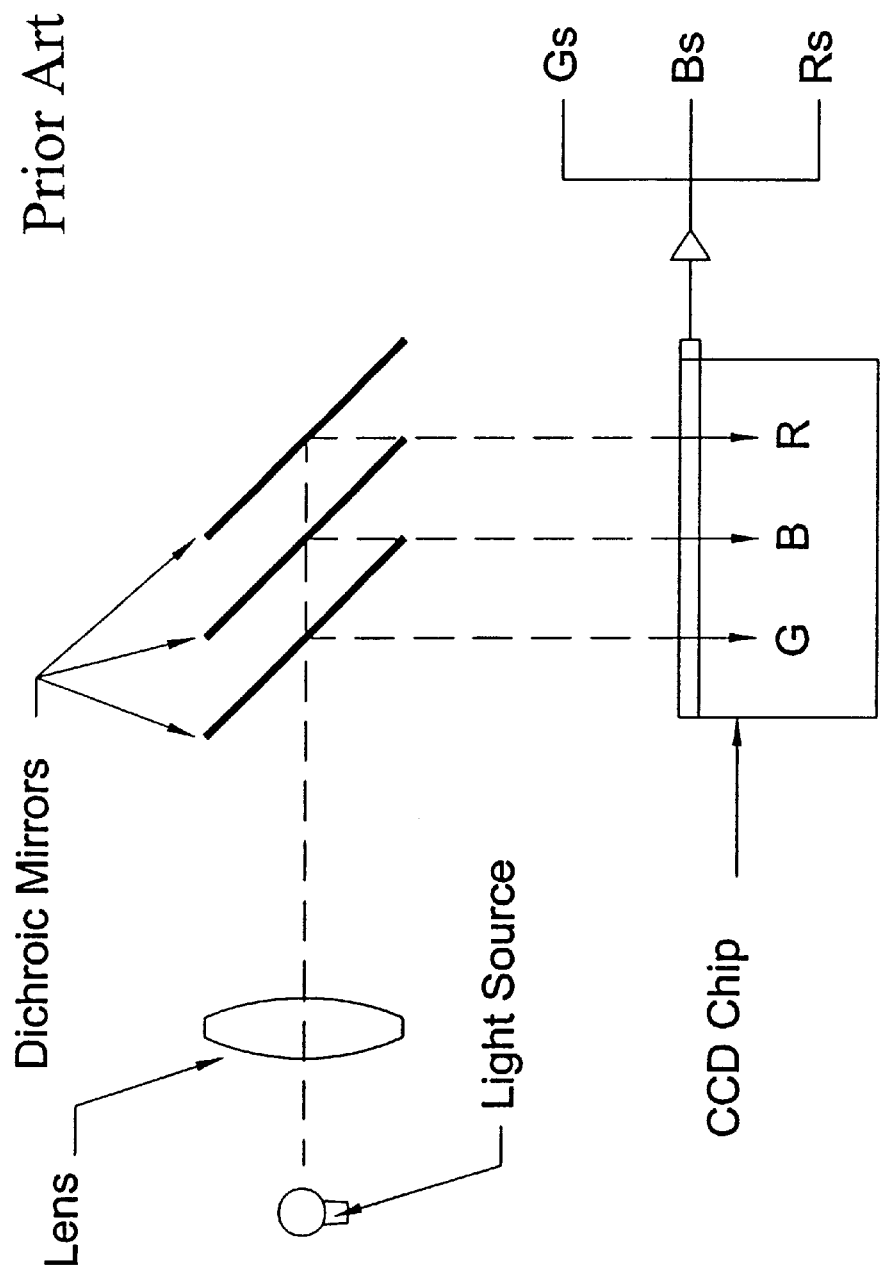
FIG. 1 is a schematic illustration of the optical path for a simple prior art instrument.
Figure 2:
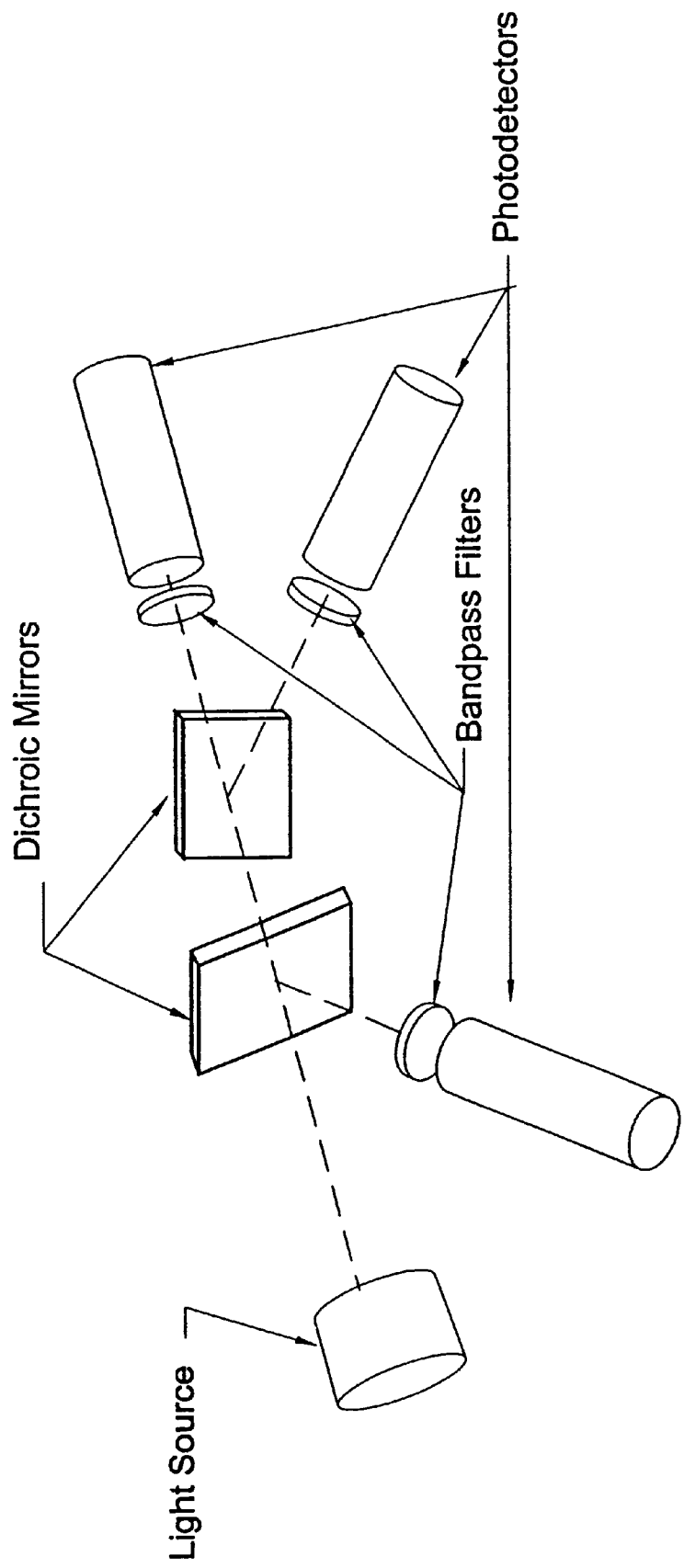
FIG. 2 is a schematic illustration of the optical path for a prior art instrument.
Figure 3:
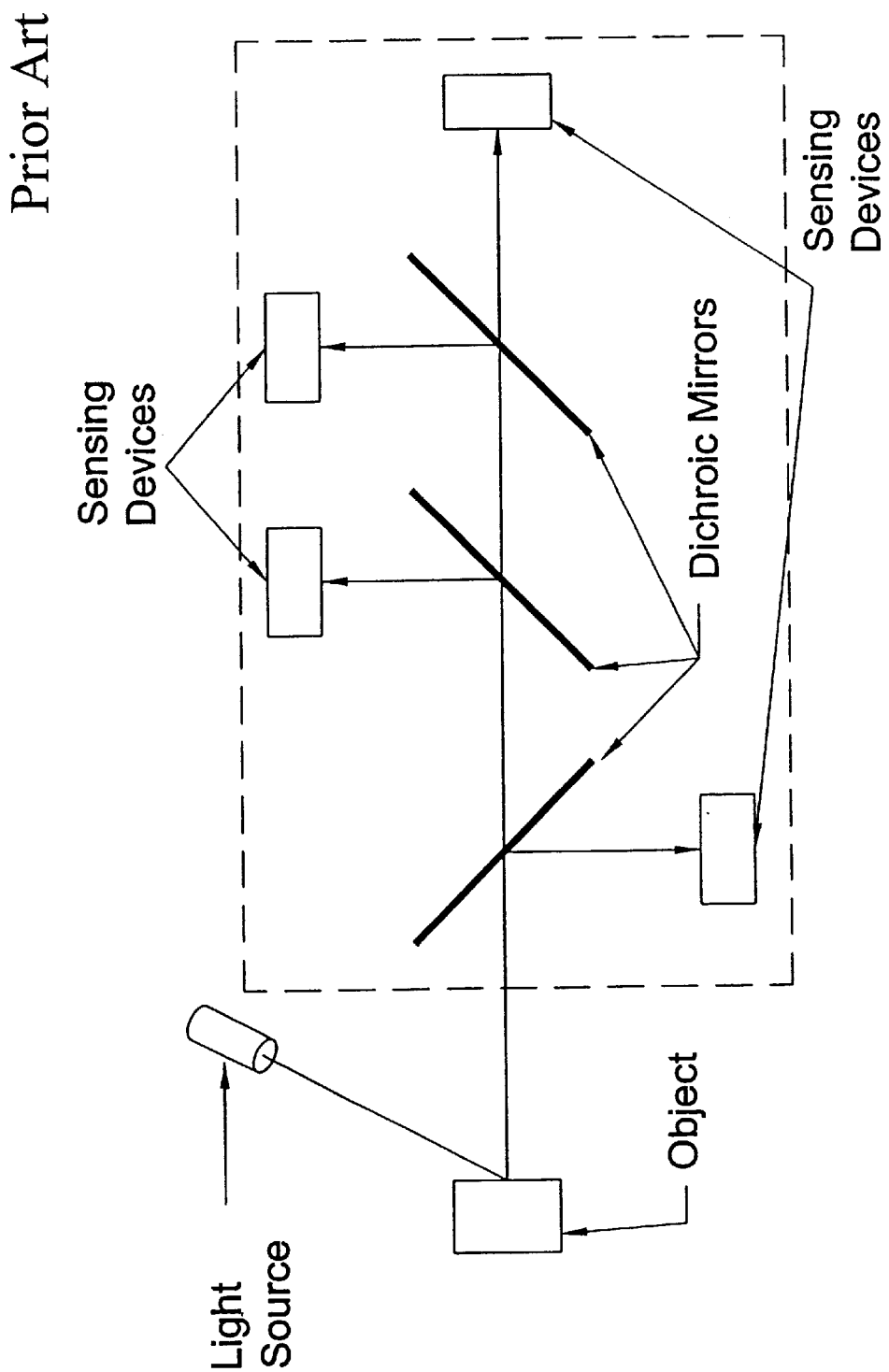
FIG. 3 is a schematic illustration of the optical path of another prior art instrument.
Figure 4:
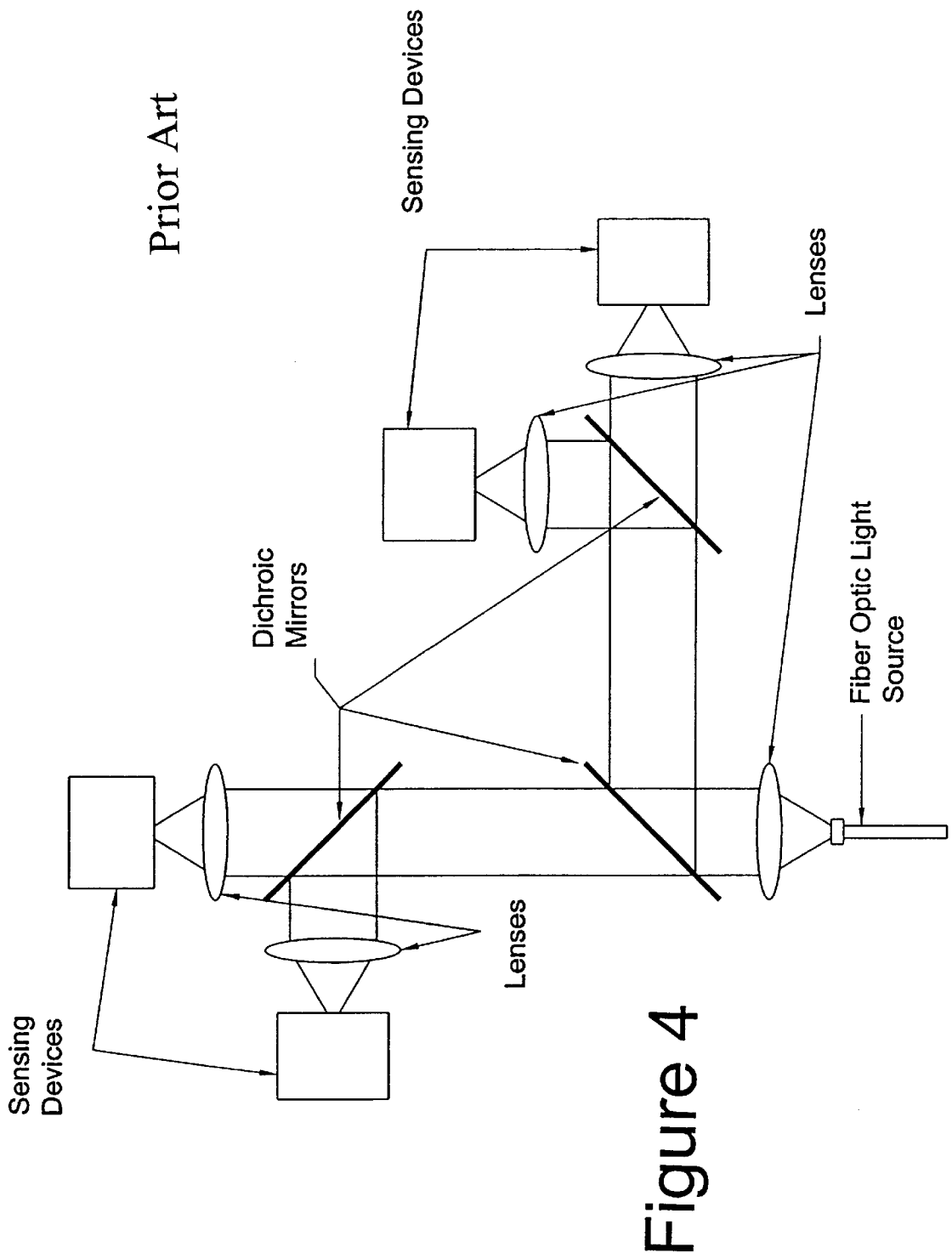
FIG. 4 is a schematic illustration of the optical path of another prior art instrument.

As shown in FIG. 1 of the aforementioned U.S. Pat. No. 5,538,613, an apparatus for detecting fluorescently-labeled molecules can include an excitation light source, such as a laser, connected through optical fiber to be directed onto a gel separation medium such as an electrophoresis gel. Light which originates from the gel is then picked up by collecting optics and conveyed to an array of dichroic mirrors. What is described in this specification is a filter module subcomponent, useful in the type of devices disclosed in said U.S. Pat. No. 5,538,613, or other similar optically based instruments in which light separation is desired. The removable filter module permits convenient changing or swapping of the dichroic mirrors so that the same instrument can be used to detect and analyze more than one fixed set of fluorescent labels.

In essence, the replaceable filter module of the present invention is intended to allow an instrument to be utilized for more than one purpose. In essence, a filter module assembly incorporating a series of dichroic mirrors can be used for one specific purpose, such as analyzing the fluorescent tags normally used with DNA sequencing. Then, the entire filter module assembly can be removed from the instrument and replaced with a second filter module assembly having dichroic mirrors of different wavelength configurations. This would enable different fluorescent tags used for other purposes to be read by the same instrument. In essence, the purpose of changing the filter modules in an instrument of this kind is to change the frequencies which are analyzed by the instrument so as to make the instrument capable of detecting fluorescence activity at any defined wavelength bands and permitting switching from one set of tests to another simply by changing a filter module corresponding to the light wavelength bands which are sought to be detected.

Figure 5:
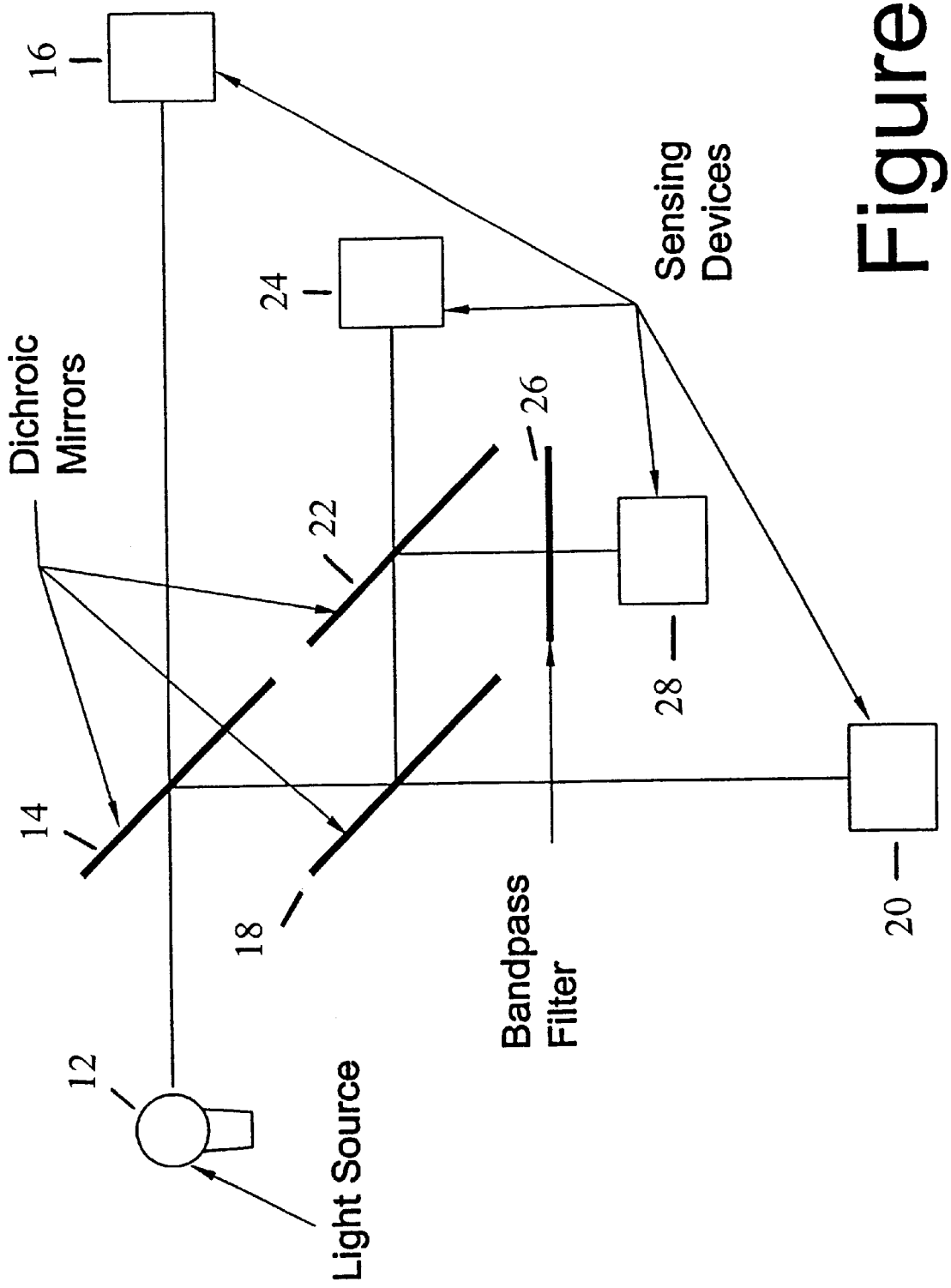
FIG. 5 is a schematic illustration of the optical path for the instrument of the present invention.

The basic optical set up for the preferred style of instrument is illustrated in FIG. 5. Light emanates from a light source 12. The light source as illustrated in FIG. 10 would, in an actual instrument, refer to the light collected from the sample, such as the fluorescence light pattern originating from an electrophoresis gel assembly, which is then directed to the optics of FIG. 6 by other conventional optical elements. The incoming light is directed to a first dichroic mirror 14. Light which is able to pass through the first dichroic mirror 14, that is which contains within it spectrum of light signals corresponding to the transmission wavelength band of the dichroic mirror 14, pass linearly through the dichroic mirror 14 and on to a photodetector 16. Light which is reflected from the dichroic mirror 14 passes to a next dichroic mirror 18. Any light incident upon the dichroic mirror 18 which fits within the wavelength band of light transmitted by the mirror is passed through the mirror to a photodetector 20. The remaining light is reflected by the dichroic mirror 18 to a dichroic mirror 22. Again, light which is incident upon the dichroic mirror 22, and which fits within the wavelength band of light which is transmitted by the dichroic mirror 22, passes on to a photodetector 24. Light which is reflected by the dichroic mirror 22 passes through a bandpass filter 26 and on to a last photodetector 28.

Thus, each dichroic mirror selectively transmits a defined wavelength region onto its respective photodetector and reflects the unused remaining wavelengths of light onto the next dichroic mirror or to the bandpass filter. The bandpass filter can be used for the last stage, instead of a dichroic mirror, since no further use is required for the rejected light. This allows simply detection of four separate color spectrums and the concept may quite easily be extended beyond four color detection by continuing the dichroic mirror cascade. Note that the first three dichroic mirrors are each angled at 45° relative to the incident light, and this geometry can be maintained indefinitely. This system does, however, require precise precisioning of the mirrors with respect to each other and with respect to the photodetectors. This is desirable because the transmission properties of the dichroic mirror are very sensitive to the angle of incidence of light incident on the mirror. In order for the dichroic mirrors to perform according to their design parameters the mirrors must be oriented at precisely 45° with respect to the incident light beam. Similarly, the optical properties of the bandpass filter are also dependent upon the angle of incidence of the fluorescent signal. As a result, the module was designed to minimize angular variation of the positioning of the filters and the module within the apparatus, by firmly fixing the dichroic mirrors in their physical relationship to each other. This is done by fixing the positions of the dichroic mirrors and the bandpass filter relative to each other in a sub-assembly. This sub-assembly can then be housed in a larger instrument in such a fashion that replacing the filter module does not alter the physical relationships between the mirrors. In other words, when it is time to swap out optical elements, the whole assembly is swapped as a fixed unit and the critical physical relationships between the mirrors are not altered.

Figure 6:
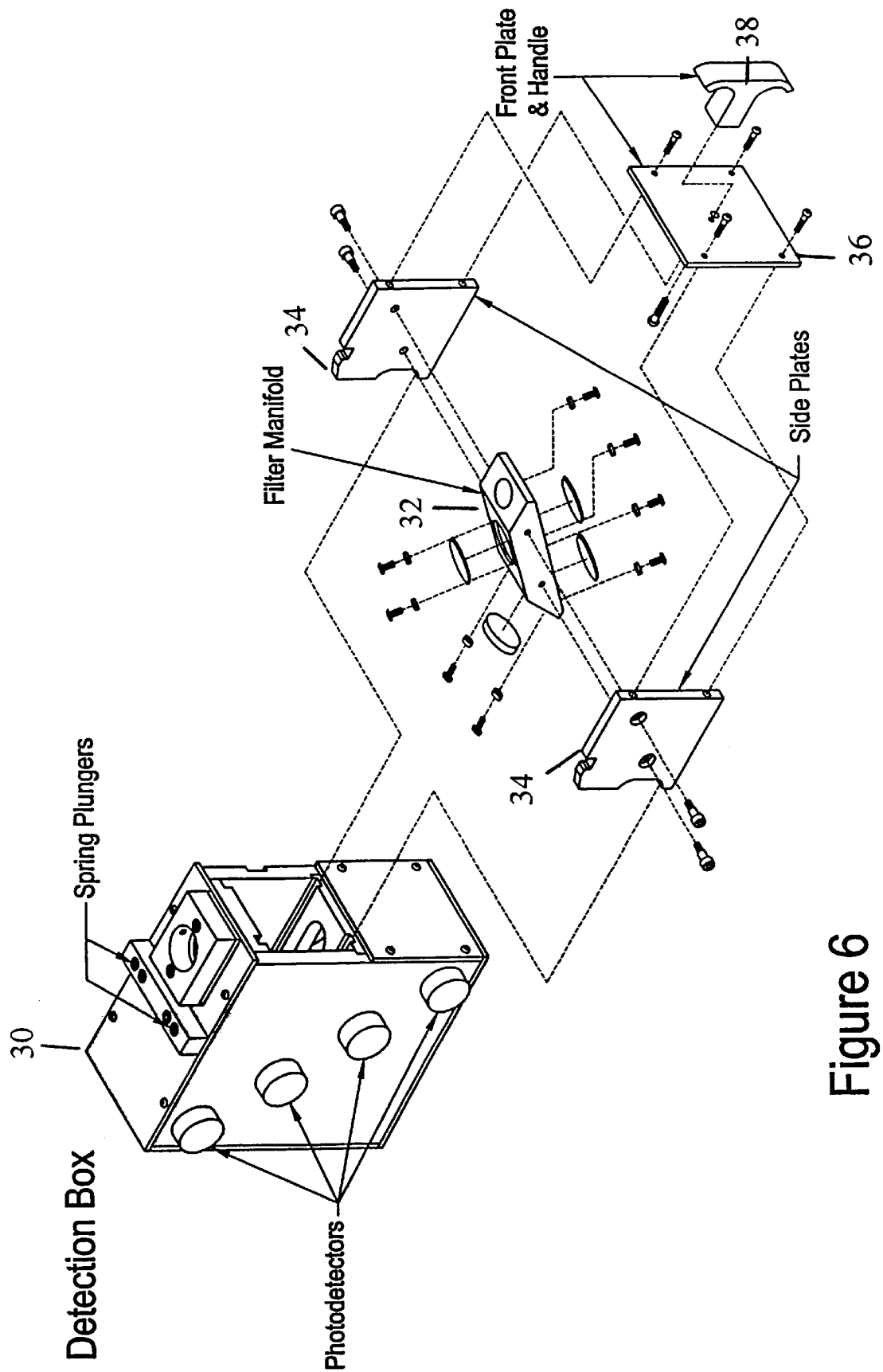
FIG. 6 is a partially expanded perspective view of a filter module according to the present invention.
Figure 7:
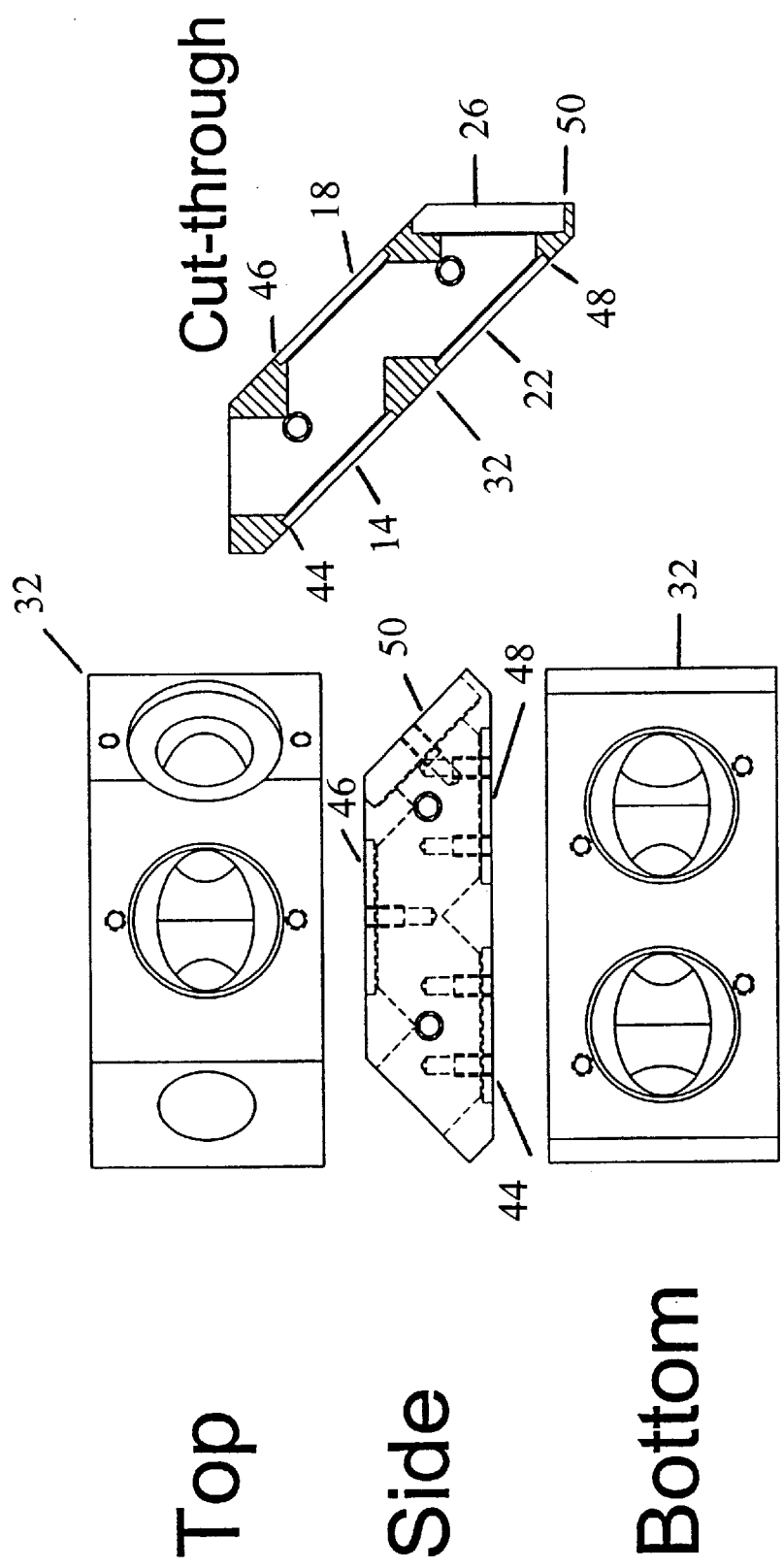
FIG. 7 show, top plan, side plan, bottom plan and cross-sectional views respectively of the filter manifold of the embodiment of FIG. 6.

This is accomplished by using a design as illustrated in FIG. 6. In FIG. 6, a detection box 30 is a housing into which the replaceable filter module, illustrated in exploded fashion in the lower right portion FIG. 6, is inserted and removed to change filter modules. Note that the filter module is constructed on a filter manifold 32 onto which each of the dichroic mirrors are independently and fixedly mounted. The filter manifold is also illustrated in greater detail in FIGS. 7A, 7B, 7C and 7D which shows the exterior views and a cross-sectional view of the filter manifold. The filter manifold 32 has a light passage 42 through its interior and four mounts for optical elements. The mounts 44, 46 and 48 are oriented at a 45° angle with respect to horizontal, and each is parallel to the others so that all the dichroic mirrors received in those mounts are parallel and aligned to transfer rejected light from each mirror to the next. The last optical element mount 50 is oriented at an angle of 45° to the other mounts, to receive the band pass filter element. The filter manifold 32 is bolted securely to side plates 34 which are in turn connected to a front plate 36, which has a handle 38 mounted on it. A suitable recess is provided inside of the detection box 30 so that the side rails 34 can support the assembled filter module, composed of the filter manifold assembly 32 with the mounting side plates 34 and the front plate 36, as it is slid in and out of the detection box 30. The detection box 30 includes mounting locations for the photodetectors and suitable conventional optic (not shown) to direct the outputs from the dichroic mirrors to the photodetectors. It is an advantage of this design that the filter manifold includes a series of fixed mounts, each of which is precisely located and sized so as to receive there within one of the dichroic mirrors in a fixed and specific relationship with regard to other dichroic mirrors and the other optics of the instrument. Since the dichroic mirrors are fixed in position, the only alignment which has to be done is the alignment of the whole filter module with the detection box to ensure that all the optics are in proper alignment.

Note that the top edges of the side plates have cuts in their top edge to make contact with spring loaded bolters inside of the detection box 30 so that the filter module can be locked in place inside the unit. This holds the filter module securely inside the detection box in use and holds the filter manifold in a fixed relationship with regard to the other optical elements contained within the detection box 30.

Removal of the filter module is accomplished simply by pulling on the handle 38. Since the slope of the detent formed in the side panels is a little steeper when withdrawing than when inserting, more force is required to remove the module to insert it. By balancing parameters such as the plunger tension the slope of the detent on the side panels, a variety of holding pressures can be achieved until one that is comfortable and optimal can be obtained.

It can be readily seen that once the filter manifold is created and each of the mirrors is mounted on to it, the dichroic mirrors and filters are assured of proper alignment with respect to one another. This is superior to a design in which each of the filters is positioned independently inside the detection apparatus since placement of each mirror is subject to positional and angular error. By attaching the filters all to a common aligning manifold, in a manner in which the mirrors can fit into the manifold in only one location and at one orientation, only the alignment of the entire module with respect to the detection apparatus needs to be of any concern.

Figure 8:
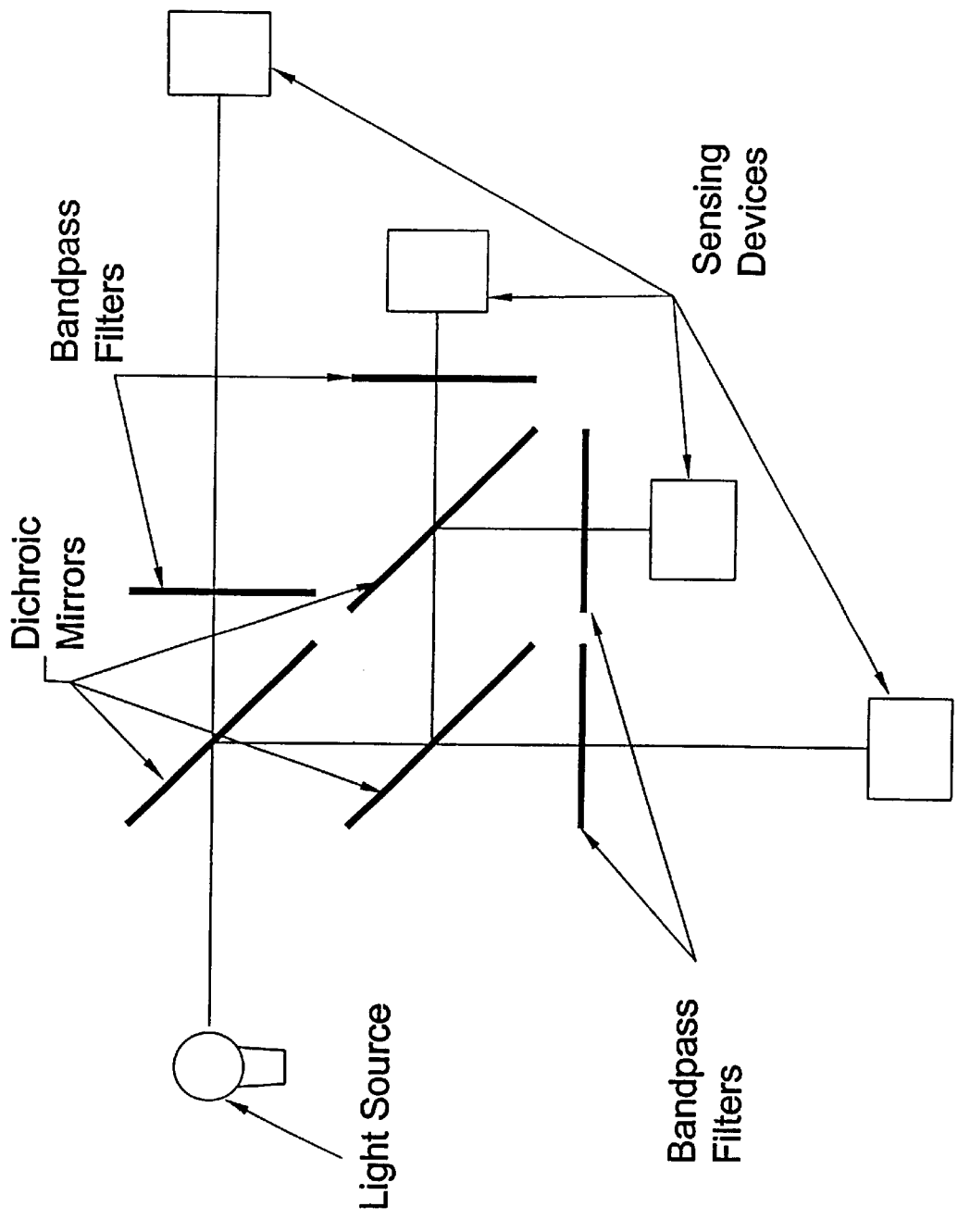
FIG. 8 is a schematic illustration of an alternative optical path for an instrument according to the present invention.

FIG. 8 illustrates the optics of an alternative embodiment of the invention in which bandpass filters are added to enhance the performance of the dichroic mirror. Since bandpass filters can be manufactured to have a very narrow band of transmission, the addition of bandpass filters to the dichroic filter module would allow more precise control over which wavelengths of light are passed onto each of the detectors. Alternatively, the dichroic mirrors could be replaced with beam splitters to separate the light signal prior to wavelength filtering. This design would require a slightly more complex part for the filter manifold, but would offer the same advantages of ease of changing optics and fixed alignments among parts. The bandpass filters are illustrated at 40 in FIG. 8. Otherwise the reference numerals refer to the same elements as in the embodiment of FIG. 5.

Figure 9:
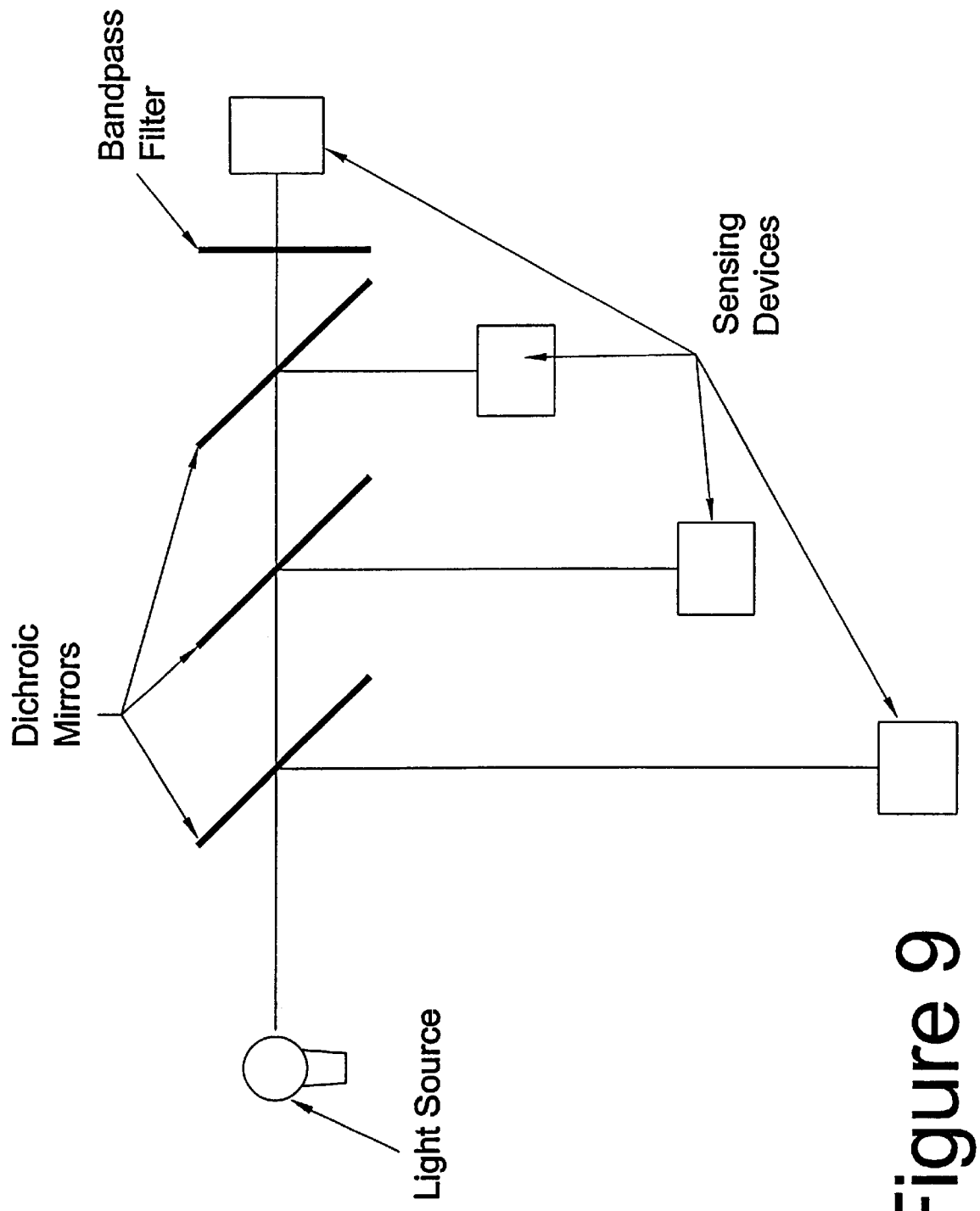
FIG. 9 is another schematic illustration of an alternative optical path for an instrument according to the present invention.

The embodiment of FIG. 9 illustrates a version where the dichroic mirrors have limited reflection bands and broad transmission bands. In this embodiment, the dichroic mirrors would reflect a limited range of wavelengths to a photodetector and pass the remaining wavelengths to subsequent mirrors. A disadvantage of this system is that the transmission of light through the dichroic mirrors is not efficient as light reflection. As a result, a significant loss of light intensity would incur if a cascade were very long. This embodiment does permit a relatively straightforward light path through the instrument however, as illustrated in FIG. 9, which would make the appropriate filter manifold relatively easy to make.

We claim:
1. An apparatus for determining the amounts of fluorophore-labeled molecules in a medium comprising:
   a. a source of fluorophore-labeled molecules, the molecules labeled with at least two different fluorophores having distinct fluorescence emission spectra;
   b. an excitation source for producing excitation light which can be directed to the fluorophore-labeled molecules;
   c. a collection device for collecting the emitted light created by the labeled molecules;
   d. an interchangeable housing which contains a plurality of filters used to separate the wavelengths of the emission spectra of the fluorophores, each interchangeable housing containing a distinct plurality of filters allowing the detection of specific emission spectra, the housing being interchangeable to change filters in the apparatus; and
   e. a plurality of detectors, each detector receiving a distinct wavelength constituent from one of the filters, each detector thus detecting a specific fluorophore-labeled molecule in the medium.

2. The apparatus of claim 1 further comprising
   a. a fixture for aligning the interchangeable housing within the apparatus such that light from the filters is directed to the detectors; and
   b. a locking mechanism to secure the housing module in the apparatus.

3. The apparatus of claim 2 wherein the fixture for aligning the plurality of filters is a single piece containing at least two intersecting channels cut in a manner allowing a precise alignment of the filters with respect to one another and with respect to external components.

4. The apparatus of claim 3 wherein the singular fixture is a trapezoidal shaped block of aluminum.

5. The apparatus of claim 3 wherein the plurality of filters is an array of dichroic mirrors aligned to receive the signal from the labeled molecules collected by the collecting device, the dichroic array including a plurality of dichroic mirrors having distinct filtering characteristics wherein the signal is separated into distinct wavelength constituents by reflection at predetermined wavelengths and transmission at other wavelengths.

6. The apparatus of claim 5 further comprising at least one bandpass filter attached to the fixture.

7. The apparatus of claim 2 wherein the housing module comprises:
   a. two side plates attached to the fixture;
   b. a front plate attached to the two side plates;
   c. a handle piece attached to the front plate;
   d. two mating channels attached to the inside of the apparatus and positioned to receive the two side plates.

8. The apparatus of claim 7 wherein the side plates are machined on their top edge to provide a detent and a sloping cut from the back edge to the detent in order to accommodate a locking mechanism.

9. The apparatus of claim 2 wherein the locking mechanism comprises spring-loaded plungers positioned precisely inside the apparatus and attached to the apparatus which compress as the side plates of the housing module are inserted into their respective mating channels until detents machined into the top edge of the side plates of the housing module are reached whereby the plungers spring back into place securing the housing module to the apparatus until the housing module is removed by the pulling of the handle piece.

10. An apparatus for scanning an electrophoretic separation medium containing fluorophore-labeled molecules comprising:
   a. an excitation source for producing excitation light directed to excite the fluorophore-labeled molecules;
   b. a collection device for collecting the emitted light created in the medium by the fluorophore-labeled molecules;
   c. an interchangeable filter module housing containing an array of dichroic mirrors aligned to receive the signal from the labeled molecules, each interchangeable filter module capable of containing a distinct array of dichroic mirrors, each dichroic array including a plurality of dichroic mirrors having distinct filtering characteristics wherein the emitted light signal is separated into distinct wavelength constituents by reflection at predetermined wavelengths and transmission at other wavelengths, the housing module being replaceable by another filter housing module while retaining the optical alignment of the apparatus; and
   d. a plurality of detectors, each detector receiving a distinct wavelength constituent from one of the dichroic mirrors, each detector thus detecting a specific labeled molecule in the medium.

11. The apparatus of claim 10 wherein the replaceable filter module comprises:
   a. a fixture for aligning the dichroic mirrors;
   b. the housing module allowing the dichroic mirror array to be removed and replaced by another housing module containing a different dichroic mirror array without disturbing the optical alignment of the detection system; and
   c. a locking mechanism to secure the housing module in the apparatus.

12. The apparatus of claim 11 wherein the fixture for aligning the dichroic mirror array is a single piece containing at least two intersecting channels cut in a manner allowing a precise alignment of the dichroic mirrors with respect to one another and with respect to external components.

13. The apparatus of claim 12 wherein the singular fixture is a trapezoidal shaped block of aluminum.

14. The apparatus of claim 13 further comprising at least one bandpass filter attached to the fixture.

15. The apparatus of claim 11 wherein the housing module comprises:
   a. two side plates attached to the fixture;
   b. a front plate attached to the two side plates;
   c. a handle piece attached to the front plate;
   d. two mating channels attached to the inside of the apparatus and positioned to receive the two side plates.

16. The apparatus of claim 15 wherein the side plates are machined on their top edge to provide a detent and a sloping cut from the back edge to the detent in order to accommodate a locking mechanism.

17. The apparatus of claim 11 wherein the locking mechanism comprises spring-loaded plungers positioned precisely inside of the apparatus and attached to the said apparatus which compress as the side plates of the housing module are inserted into their respective mating channels until detents machined into the top edge of the side plates of the housing module are reached whereby the plungers spring back into place securing the housing module to the optical detection device until said housing module is removed by the pulling of the handle piece.

* * * * *